United States Patent
Hoyt et al.

(10) Patent No.: US 8,267,865 B2
(45) Date of Patent: Sep. 18, 2012

(54) SONOELASTOGRAPHIC SHEAR VELOCITY IMAGING USING CRAWLING WAVE EXCITATION

(75) Inventors: Kenneth Hoyt, Rochester, NY (US); Kevin J. Parker, Rochester, NY (US)

(73) Assignee: University of Rochester, Rochester, NY (US)

( * ) Notice: Subject to any disclaimer, the term of this patent is extended or adjusted under 35 U.S.C. 154(b) by 772 days.

(21) Appl. No.: 12/032,364

(22) Filed: Feb. 15, 2008

(65) Prior Publication Data

US 2008/0200805 A1 Aug. 21, 2008

Related U.S. Application Data

(60) Provisional application No. 60/901,643, filed on Feb. 16, 2007.

(51) Int. Cl.
*A61B 5/00* (2006.01)
*A61B 8/00* (2006.01)

(52) U.S. Cl. ............ 600/438; 600/437; 73/584; 73/597

(58) Field of Classification Search .................. 600/438; 73/597, 602, 861.06
See application file for complete search history.

(56) References Cited

U.S. PATENT DOCUMENTS

| | | | |
|---|---|---|---|
| 6,764,448 B2* | 7/2004 | Nightingale et al. | 600/437 |
| 7,444,875 B1* | 11/2008 | Wu et al. | 600/438 |
| 2005/0054930 A1* | 3/2005 | Rickets et al. | 600/453 |
| 2005/0203398 A1* | 9/2005 | Sandrin et al. | 600/438 |
| 2006/0274928 A1 | 12/2006 | Collins et al. | |
| 2007/0016031 A1 | 1/2007 | Mourad et al. | |

OTHER PUBLICATIONS

Wu, Zhe. Shear Wave Interferometry and Holography, an Application of Sonoelastography. Aug. 23, 2005. Rochester Center for Biomedical Ultrasound. http://hdl.handle.net/1802/1967.*
Shamdasani, V.; Kim, Y.; , "Two-dimensional autocorrelation method for ultrasound-based strain estimation," Engineering in Medicine and Biology Society, 2004. IEMBS '04. 26th Annual International Conference of the IEEE , vol. 1, no., pp. 1380-1383, Sep. 1-5, 2004 doi: 10.1109/IEMBS.2004.1403430.*
Loupas, T.; Powers, J.T.; Gill, R.W.; , "An axial velocity estimator for ultrasound blood flow imaging, based on a full evaluation of the Doppler equation by means of a two-dimensional autocorrelation approach," Ultrasonics, Ferroelectrics and Frequency Control, IEEE Transactions on , vol. 42, No. 4, pp. 672-688, Jul. 1995 doi: 10.1109/58.393110.*
Taylor et al. "Three-dimensional sonoelastography: principles and practices". Phys. Med. Biol. 45 (2000) 1477-1494.*
Hoyt, K., "Sonoelastographic Shear Velocity Imaging: Experiments on Tissue Phantom and Prostate," 2006 IEEE Ultrasonics Symposium, Vancouver, pp. 1686-1689.

* cited by examiner

*Primary Examiner* — Brian Casler
*Assistant Examiner* — Phong K Huynh
(74) *Attorney, Agent, or Firm* — William Greener; Bond, Schoeneck & King, PLLC

(57) ABSTRACT

Vibration sources are applied to a body or other object to image a region of interest. The mechanical vibrations introduced by the sources interfere in the region of interest to produce a crawling wave, which is detected by an ultrasound probe A relationship between crawling wave phase derivatives and local shear wave velocity is derived with phase derivatives estimated using either one-dimensional (1D) or two-dimensional (2D) autocorrelation-based techniques to image the region of interest.

13 Claims, 2 Drawing Sheets

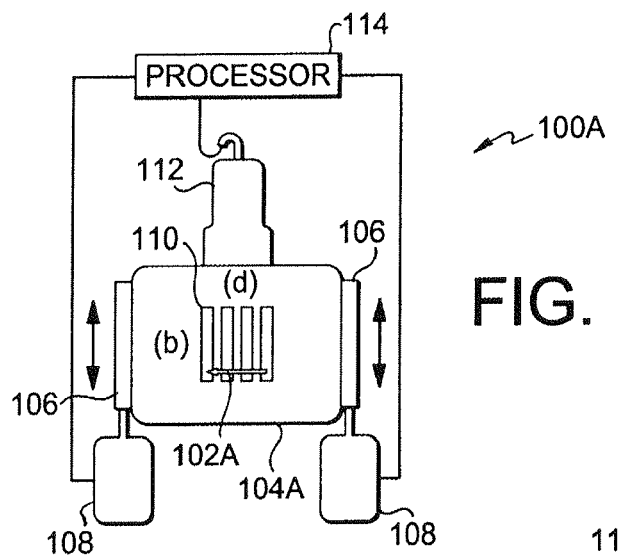
FIG. 1A
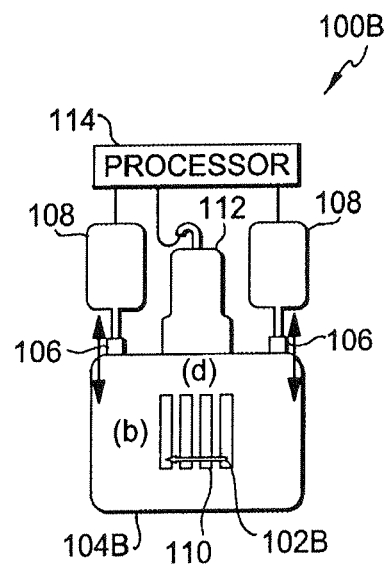
FIG. 1B
FIG. 2
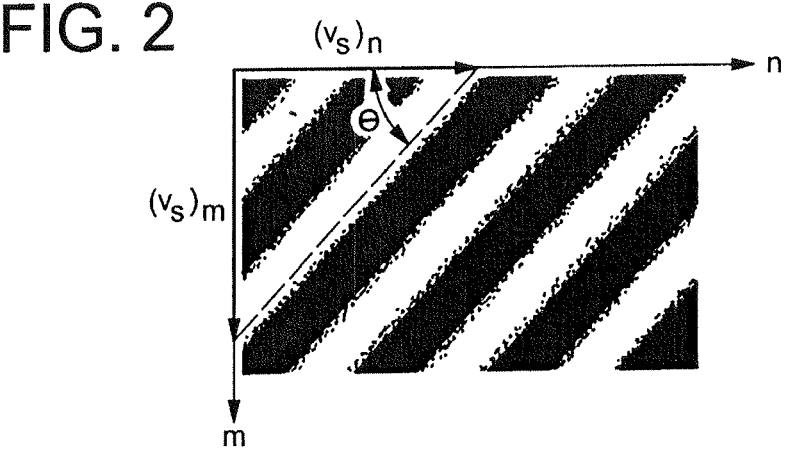

SONOELASTOGRAPHIC SHEAR VELOCITY IMAGING USING CRAWLING WAVE EXCITATION

REFERENCE TO RELATED APPLICATION

The present application claims the benefit of U.S. Provisional Patent Application No. 60/901,643, filed Feb. 16, 2007, whose disclosure is hereby incorporated by reference in its entirety into the present disclosure.

STATEMENT OF GOVERNMENT INTEREST

The work leading to the present invention was supported by NIH Grant No. 5 R01 AG16317-05. The government has certain rights in the invention.

FIELD OF THE INVENTION

The present invention is directed to sonoelastography and more particularly to sonoelastography using interfering shear waves to produce crawling waves.

DESCRIPTION OF RELATED ART

Vibrational sonoelastography is a tissue elasticity imaging technique, developed at the University of Rochester, which estimates the amplitude response of tissues under harmonic mechanical excitation using ultrasonic Doppler techniques. Due to a mathematical relationship between particle vibrational response and received Doppler spectral variance, low frequency (50 to 500 Hz) and low amplitude (1 to 100 μm) shear waves propagating in tissue can be visualized using sonoelastography to detect regions of abnormal stiffness. Low frequency shear waves are used because they are much less attenuated (due to damping mechanisms) than at higher frequencies. Furthermore, given the shear moduli distribution typically encountered in soft tissue (more than four orders of magnitude), corresponding wavelengths reside in the useful range of millimeters.

Recently, it was shown that interfering shear waves produce slowly propagating interference patterns with an apparent velocity much less than (but proportional to) the underlying true shear velocity. Termed crawling waves, they are generated using a pair of mechanical sources vibrating at slightly offset frequencies or by continuously phase shifting one of the source excitation signals.

Sonoelastographic imaging of interference patterns has been used for estimation of the shear velocity of homogeneous biomaterials. However, before the present invention, it had not been used for imaging of heterogeneous biomaterials.

SUMMARY OF THE INVENTION

It is therefore an object of the invention to achieve such imaging.

To achieve the above and other objects, the present invention is directed to a novel real-time sonoelastographic technique for estimating local shear velocities from crawling wave images. Specifically, a relationship between crawling wave phase derivatives and local shear wave velocity is derived with phase derivatives estimated using either one-dimensional (1D) or two-dimensional (2D) autocorrelation-based techniques. In comparison, the 1D sonoelastographic shear velocity estimator has the advantage of being computationally simple, whereas the 2D estimation technique provides enhanced performance in terms of minimizing noise artifacts. Thus, a fundamental tradeoff between computational time and estimator performance distinguishes these two dedicated shear velocity estimation and imaging algorithms.

The shear wave interference patterns can be visualized in real-time using sonoelastographic imaging techniques. In general, crawling wave images describe shear wave propagation patterns and allow local estimation of shear velocity distributions. Assuming that the local shear velocity values are proportional to the square root of the shear modulus, spatial mapping of either parameter allows production of quantitative tissue elasticity images.

The experimental setup is centered on an ultrasound scanner modified for sonoelastographic imaging that allows real-time visualization of crawling wave sonoelastograms. Furthermore, sonoelastographic data, either image or demodulated data sets (i.e. in-phase and quadrature signals), are utilized for processing shear velocity sonoelastograms.

Two or more (preferably two) vibration sources are utilized to excite shear wave propagation and to generate shear wave interference patterns (i.e., crawling waves). These sources (or active vibration regions) are placed in appropriate locations, such as in direct contact with opposing lateral boundaries of the biomaterial with the long axis (and induced shear vibration) parallel to, and in line with, the desired image plane (governed by transducer positioning). Vibration can be achieved in a variety of ways, e.g., using external vibration sources in contact with the tissue, or using an acoustic radiation force on each side of the region of interest to generate the interference patterns. A two-channel signal generator produces two monochrome low frequency signals that are typically amplified before being input to the vibration sources. Introducing a frequency offset or phase shifting one of the vibration excitation signals allows spatial translation of shear wave interference patterns (i.e., crawling waves) across the image plane. If the delta frequency of the vibration sources becomes zero or very small, then the crawling wave becomes a fixed interference pattern. Such a fixed interference pattern can also be used with the 1D and 2D estimators of the present invention.

Additional disclosure is found in the following publications, which are hereby incorporated by reference in their entireties into the present disclosure:

K. Hoyt et al, "Feasibility of Two-Dimensional Quantitative Sonoelastographic Imaging," *IEEE Ultrasonics Symposium* 2007, pp. 2032-2035;

K. Hoyt et al, "Lesion contrast and detection using sonoelastographic shear velocity imaging: Preliminary results," *Proc. Of SPIE* Vol. 6513, 65130L (2007), pp. 65130L-1 to -8;

K. Hoyt et al, "Muscle Tissue Characterization Using Quantitative Sonoelastography: Preliminary Results," *IEEE Ultrasonics Symposium* 2007, pp. 365-368;

K. Hoyt et al, "Real-Time Shear Velocity Imaging Using Sonoelastographic Techniques," *Ultrasound in Med. & Biol.*, Vol. 33, No. 7, pp. 1086-1097, 2007;

K. Hoyt et al, "Sonoelastographic Shear Velocity Imaging: Experiments on Tissue Phantom and Prostate," 2006 *IEEE Ultrasonics Symposium*, pp. 1686-1689; and K. Hoyt et al, "Two-Dimensional Sonoelastographic Shear Velocity Imaging," *Ultrasound in Med. & Biol.* Vol. 33, 2007.

BRIEF DESCRIPTION OF THE DRAWINGS

Preferred embodiments of the invention will be set forth in detail with reference to the drawings, in which:

FIGS. 1A and 1B show setups for carrying out the preferred embodiments;

FIG. 2 shows mean shear velocity vectors in relation to a representative shear wave interference pattern.

DETAILED DESCRIPTION OF THE PREFERRED EMBODIMENTS

Figure 3:
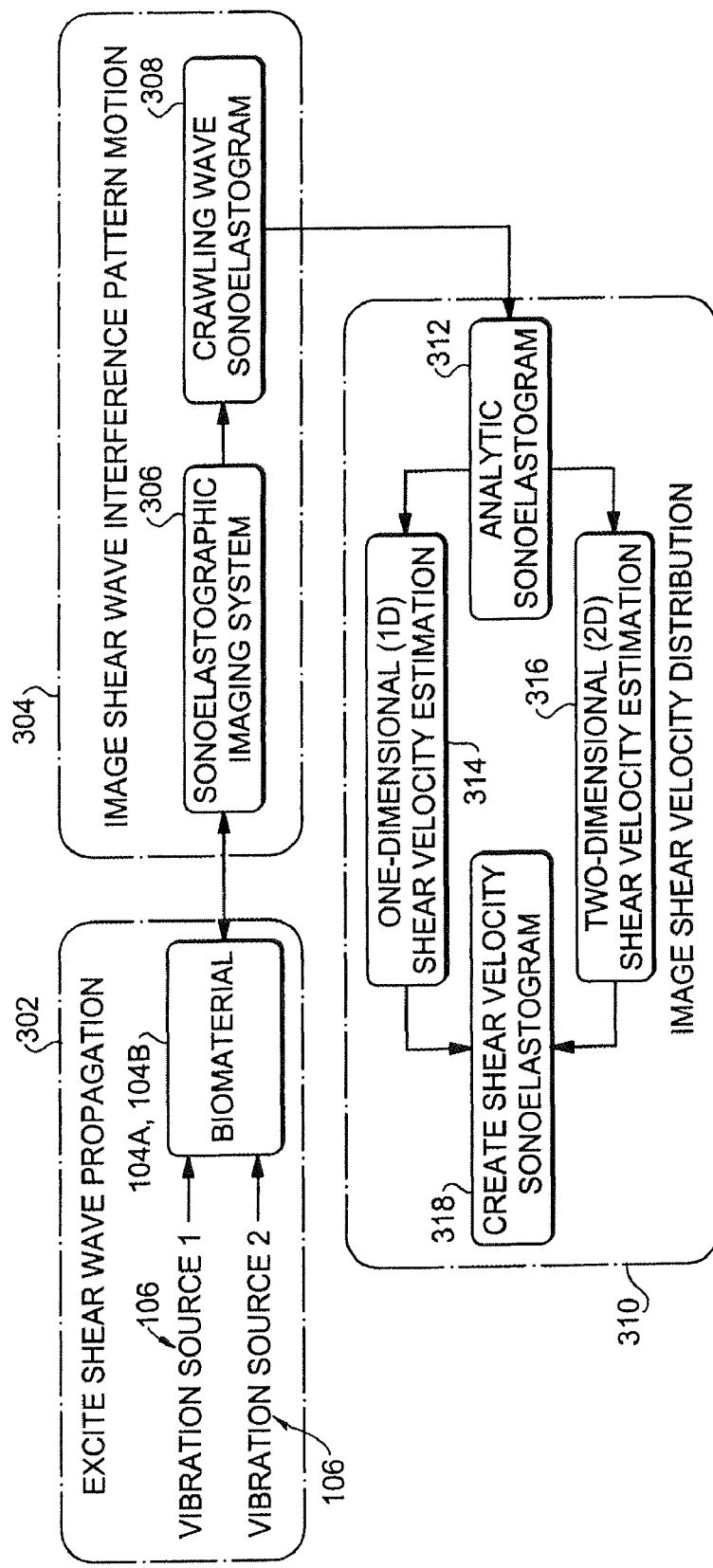
FIG. 3 shows an overview of the operational steps of the preferred embodiments.

Preferred embodiments of the invention will now be set forth in detail with reference to the drawings, in which like reference numerals refer to like elements or steps throughout.

FIGS. 1A and 1B show setups for ex vivo and in vivo imaging, respectively. The ex vivo imaging setup 100A images a region of interest 102A in an object 104A by applying two mechanical sources 106 under the control of controllers 108 to be coupled to the tissue surface. The mechanical sources 106 are driven at slightly offset frequencies such that they interfere in the region of interest to produce a crawling wave 110. The crawling wave 110 is detected by an ultrasound probe 112 in communication with a processor 114 for performing the processes to be described below. The processor can also control the controllers 108. The in vivo imaging setup 100B differs in that the mechanical sources 106 and probe 112 are attached to a common side of the object 104A to cause the crawling wave 110 in the region of interest 102B.

Shear wave interference displacement fields u(m, n) excited using a pair of monochromatic mechanical sources can be expressed as standing wave patterns:

$$u(m,n) = 2A^2 \exp(-\alpha D)[\cos h(2\alpha n T_n) + \cos(2k_s n T_n + \Delta k_s n T_n)] \quad (1)$$

where m and n are integer values denoting row and column matrix indices (i.e., spatial coordinates), respectively, A is the excitation source amplitude, $\alpha$ is the shear wave attenuation coefficient, D is the excitation source separation distance, $T_n$ denotes the spatial sampling interval along the n-axis (i.e., shear wave propagation axis or lateral direction), and $k_s$ and $\Delta k_s$ denote the shear wave number and difference, respectively. Note that eqn (1) assumes that the shear wave displacement data are parallel to a line of sight connecting the vibration sources. Moreover, eqn (1) assumes plane wave conditions and can be realized in practice by imaging in the far field of the shear wave sources. For discrete shear wave displacement data, the analytic signal û(m, n) of u(m, n) is defined as:

$$\hat{u}(m,n) = u(m,n) - j\breve{u}(m,n) \quad (2)$$

where ŭ(m, n) denotes the discrete 1D Hilbert transform of û(m, n) along the n-axis $$\breve{u}(m, n) = \frac{-1}{\pi n} u(m, n) \quad (3)$$

The shear velocity in 1D space can be estimated by evaluating the phase of the 1D autocorrelation function $\hat{\gamma}(n')$ of the analytic signal û(m, n):

$$\hat{\gamma}(n') = \sum_{n=0}^{N-n'-1} \hat{u}*(n)\hat{u}(n+n') \quad (4)$$

at lag n'=1 and where * denotes the complex conjugation operator. For the above discussion, it has been assumed that the observation window consists of N lateral discrete samples (n=0, 1, . . . , N−1), i.e., the data kernel is taken parallel to the shear wave interference pattern axis. Finally, the 1D mean shear velocity estimate $\langle v_s \rangle_{1D}$ is given as follows:

$$\langle v_s \rangle_{1D} = \frac{2\pi(2f_s + \Delta f_s)T_n}{\tan^{-1}\left\{\frac{\text{Im}[\hat{\gamma}(1)]}{\text{Re}[\hat{\gamma}(1)]}\right\}} \quad (5)$$

which indicates that the local shear velocity can be estimated from spatial shear wave interference patterns (or crawling wave image frame) given knowledge of the source vibration frequencies and spatial sampling rate. Since eqn (5) produces a local shear velocity estimate, 2D spatial distributions (for a given region-of-interest) are obtained by one-sample shifting the kernel throughout the shear wave displacement field. The resultant matrix is imaged and termed a shear velocity sonoelastogram.

Analogous to the approach just introduced, the shear velocity in 2D space can be estimated by evaluating the phase of the 2D autocorrelation function $\hat{\gamma}(m',n')$ of the analytic signal û(m,n):

$$\hat{\gamma}(m', n') = \sum_{m=0}^{M-m'-1} \sum_{n=0}^{N-n'-1} \hat{u}*(m,n)\hat{u}(m+m', n+n') \quad (6)$$

at lags (m'=1, n'=0) and (m'=0, n'=1), Equation (6) assumes that the observation window consists of M axial samples (m=0, 1, . . . , M−1) and N lateral samples (n=0, 1, . . . , N−1). Lastly, the mean shear velocities $\langle v_s \rangle_m$ and $\langle v_s \rangle_n$, as estimated independently and relative to the m-axis and n-axis, respectively, are given by the following expressions:

$$\langle v_s \rangle_m = \frac{2\pi(2f_s + \Delta f_s)T_m}{\tan^{-1}\left\{\frac{\text{Im}[\hat{\gamma}(1,0)]}{\text{Re}[\hat{\gamma}(1,0)]}\right\}} \quad (7)$$

and $$\langle v_s \rangle_n = \frac{2\pi(2f_s + \Delta f_s)T_n}{\tan^{-1}\left\{\frac{\text{Im}[\hat{\gamma}(0,1)]}{\text{Re}[\hat{\gamma}(0,1)]}\right\}}$$

where $T_m$ denotes the spatial sampling interval along the m-axis (i.e., longitudinal direction).

Consideration of eqns (7) and (8) allows definition an angular component $\theta$ (see FIG. 2, showing a two-dimensional description of the mean shear velocity vectors in relation to a representative shear wave interference pattern):

$$\theta = \tan^{-1}\left(\frac{\langle v_s \rangle_m}{\langle v_s \rangle_n}\right) \quad (9)$$

Introduction of eqn (9) allows realization of a 2D mean shear velocity estimate $\langle v_s \rangle_{2D}$ by projecting the 2D shear velocity vector onto the n-axis:

$$\langle v_s \rangle_{2D} = \langle v_s \rangle_n \sin \theta \quad (10)$$

Furthermore, by following the trigonometric relationship $$\tan^{-1} x = \sin^{-1}\left(\frac{x}{\sqrt{x^2+1}}\right) \quad (11)$$

combining eqns (9), (10) and (11) results in the following expression:

$$\langle v_s \rangle_{2D} = \frac{\langle v_s \rangle_m}{\sqrt{\left(\frac{\langle v_s \rangle_m}{\langle v_s \rangle_n}\right)^2 + 1}} \quad (12)$$

indicating that the 2D local shear velocity can be estimated from the spatial shear wave interference patterns given knowledge of the source vibration frequencies and spatial sampling rate. In the derivation of eqn (12) we assume that within the region defined by our kernel size that the tissue property is approximately homogeneous and that the shear wave interference patterns can be approximated as plane waves. Since eqn (12) produces a local shear velocity estimate, 2D spatial distributions are obtained by one-sample shifting the kernel throughout the shear wave displacement field.

A summary of the shear velocity imaging strategies outlined in the above sections is illustrated schematically in FIG. 3. In step 302, the shear wave propagation is excited using the vibration sources 1 and 2 (106) to the biomaterial 104A or 104B. In step 304 of imaging the shear wave interference pattern motion, a sonoeleastographic imaging system 306 produces a crawling wave sonoelastogram 308. In step 310 of imaging the shear velocity distribution, an analytic sonoelastogram 312 is formed as described above and is applied to 1D shear velocity estimation 314 or 2D shear velocity estimation 316 to produce a shear velocity sonoelastogram 318. Notice that the only major difference between the 1D and 2D shear velocity imaging techniques is in the numerical techniques utilized to process the analytic crawling wave sonoelastograms. Although the developed estimation technique is premised on crawling wave excitation, this novel real-time autocorrelation-based technique can be modified for processing and imaging tissue elasticity information from data acquired using holographic wave excitation and magnetic resonance elastography (MRE). In general, where changes in spatially varying shear wave displacement feeds are imaged and governed by the true underlying biomaterial elastic properties.

The invention has been shown to be useful in lesion contrast and detection and in muscle tissue characterization.

While preferred embodiments of the present invention have been set forth above, those skilled in the art who have reviewed the present disclosure will readily appreciate that other embodiments can be realized within the scope of the invention. For example, numerical values are illustrative rather than limiting, as are disclosures of specific uses. Therefore, the present invention should be construed as limited only by the appended claims.

What is claimed is:

1. A system for forming an image of a region of interest in an object, the region of interest comprising areas having differing elastic properties, the system comprising:

a plurality of vibration sources to generate a sinusoidal steady state interference-based crawling wave in the object;

a vibration detector that detects an interference field of the crawling wave; and a processor, coupled to the detector, characterized in that the processor controls the formation of the crawling wave, and determines a shear wave speed distribution from the crawling wave by deriving an interference field of the crawling wave and performing a two-dimensional spatial autocorrelation on the interference field.

2. A method for determining a local shear wave velocity in a sample, comprising the steps of:
   a) generating a crawling wave in the sample from a sinusoidal steady state shear wave interference;
   b) detecting an interference field of the crawling wave;
   c) performing a two-dimensional spatial autocorrelation on the interference field;
   d) using the autocorrelation to estimate a phase derivative of the crawling wave; and
   e) using the phase derivative of the crawling wave to estimate the local shear wave velocity in the sample.

3. The method of claim 2, further involving obtaining a two-dimensional (2-D) shear wave velocity spatial distribution in a given sample region by performing a one sample shifting of the crawling wave interference field and generating a resultant matrix.

4. The method of claim 3, further involving generating a shear wave sonoelastogram by imaging the resultant matrix.

5. The method of claim 2, wherein step (c) further involves performing the two-dimensional spatial autocorrelation on the detected crawling wave interference field to estimate the local shear wave velocity in two dimensional space in the sample.

6. The method of claim 5, further involving independently estimating a mean axial shear velocity and a mean lateral shear velocity relative to respective, orthogonal axial (vertical) and lateral (horizontal) axes.

7. The method of claim 6, further involving combining the axial and the lateral shear wave velocity estimates to obtain a 2-D mean shear velocity estimate.

8. The method of claim 7, further involving performing a one sample shifting of the crawling wave interference field and generating a resultant matrix.

9. The method of claim 8, further involving generating a shear wave sonoelastogram by imaging the resultant matrix.

10. The method of claim 2, further comprising using a received Doppler spectral variance to calculate the crawling wave interference field.

11. The method of claim 2, further comprising using a pair of vibrational sources having different frequencies to generate the crawling wave.

12. The method of claim 2, further comprising using a pair of vibrational sources having different frequencies and continuously phase shifting at least one sample excitation signal to generate the crawling wave.

13. The method of claim 2, wherein step (a) comprises applying the pair of vibrational sources to the object on opposite sides of the region of interest.

\* \* \* \* \*